United States Patent [19]

Palmer et al.

[11] Patent Number: 5,830,150
[45] Date of Patent: Nov. 3, 1998

[54] METHOD AND APPARATUS FOR DISPLAYING DATA

[75] Inventors: Douglas A. Palmer; N. Ty Smith, both of San Diego, Calif.

[73] Assignee: Marquette Electronics, Inc., Milwaukee, Wis.

[21] Appl. No.: 715,602

[22] Filed: Sep. 18, 1996

[51] Int. Cl.[6] ............................................. A61B 5/0402
[52] U.S. Cl. ............................................................ 600/523
[58] Field of Search .................................. 600/523, 508, 600/509

[56] References Cited

U.S. PATENT DOCUMENTS 5,622,178  4/1997  Gilham ................................. 128/710

*Primary Examiner*—Scott M. Getzow
*Attorney, Agent, or Firm*—Michael Best & Friedrich LLP

[57] ABSTRACT

A method and apparatus for simultaneously displaying a plurality of time variables indicative of the condition of a dynamic system. The system is constructed and arranged to be coupled to an array of sensors each positioned for sensing a discreet signal functionally related to one of the variables and includes an acquisition module coupled to the sensors for generating time variable signals indicative of the variables, a sorter for sorting the data into rows, and a processor receiving the rows of data and for computing a function for each variable, and means for determining a color coded plot value for each computed function.

45 Claims, 6 Drawing Sheets

| | Fig. 5 |
|---|---|
| 0.00 | |
| 0.99 | Hb sat Aorta (SpO2) |
| 0.91 | Hb sat vena cava (SvO2) |
| 15.52 | Cardiac output - Aorta (l/) |
| 82.99 | Heart rate (beats/sec) |
| 109.24 | Mean arterial pressure |

| | Fig. 6 |
|---|---|
| 5.42 | Central venous pressure |
| 86.76 | Arterial systolic press |
| 53.20 | Arterial diastolic pres |
| 0.19 | Depth of anesthesia |
| 0.98 | Neuromuscular block lev |

| | Fig. 7 |
|---|---|
| 0.00 | Tidal volume (ml) |
| 0.00 | Intrapleural pressure |
| 23.68 | Ventilator pressure |
| 0.00 | Vol% O2 in lung |
| 0.38 | Vol% O2 in mouth |
| 0.37 | |

METHOD AND APPARATUS FOR DISPLAYING DATA

BACKGROUND OF THE INVENTION

This invention relates to a method and apparatus for displaying data and more particularly for displaying physiological data.

There are numerous applications in which it is necessary to monitor multiple continuously varying input signals in order to maintain optimum conditions in a system or to respond to or anticipate emergency situations. Examples of such applications include the operation of aircraft, flight control tower systems, nuclear power plants, electrical grids, complex industrial processes and medical patient monitoring. In each case, decisions regarding procedures to be undertaken are made in response to multiple input data streams, each indicative of a critical variable.

Medical patient monitors are typically employed by physicians and other health care providers for monitoring patients in the operating room, intensive care units and emergency rooms. Monitors used in operating rooms may, for example, display such variables as blood oxygen saturation in the arterial and venous vessels, cardiac output, heart rate, mean arterial pressure, central venous pressure, arterial systolic pressure, arterial diastolic pressure, tracheal gas flow, ventilator pressure, and the volume percentage of oxygen and $CO_2$ in the patient's mouth. An array of sensors are connected to the patient for acquiring such data which is displayed on the screen of a monitor either in graphic or numeric form. Such data may also be recorded or displayed on analog or digital strip chart recorders, in colored inks, spread sheets and plotting programs, such as Cricket Graph, Excel and Delta Graph. In prior patient monitoring systems, it was necessary for the user to scan the various graphic and/or numeric displays in order to monitor the patient's condition, and to determine the occurrence of significant events which may require immediate attention and to quickly establish a priority of action. Some variables may be measured directly, such as arterial systolic and diastolic pressure and gas flow. Other variables are calculated, such as, heart rate, hemoglobin oxygen saturation, which is determined from an expression based on the amount of light at different wave lengths that is absorbed by the patient's arerial hemoglobin.

These prior art monitoring systems require that the operator scan and detect significant changes in a large number of simultaneously displayed variables, often on or from different screens because the number of necessary variables cannot be displayed on a single screen.

SUMMARY OF THE INVENTION

It is an object of the invention to provide a new and improved system for simultaneously graphically displaying multiple variables with respect to time from a dynamic system.

Another object of the invention is to simultaneously graphically display time varying data on a real time basis from an array of sensors.

A still further object of the invention is to provide a system which permits a large number of variables to be displayed simultaneously on a single screen and yet permit the rapid easy detection of important changes in one or more of the variables.

Another object of the invention is to provide a system which permits a rapid and accurate assessment of the relationship between a plurality of simultaneously displayed variables.

In general terms, the invention comprises a combination for simultaneously displaying a plurality of variables indicative of the condition of a dynamic system, the combination being constructed and arranged to be coupled to a plurality of sensors or a memory for sensing discreet signals each functionally related to one of the variables. The combination comprises means for receiving the signals and for generating time variable signals indicative of variables from each of the signals, a means for separately and simultaneously displaying each of the variables in a graphic form on a display screen in a time correlated relation and means for emphasizing variations in the values by differences in color shade.

According to one aspect of the invention, the combination includes means for varying the color of each of the displayed variables in relation to the magnitude of the signal, the signals being displayed in separate colorized bars and/or line graphs, where the magnitude of each variable determines the shade of the color.

According to another aspect, the variables are plotted graphically with the background and the fill each being displayed in a different color, or the fill may be colorized to reflect variations in amplitude as a different color shade.

According to a further aspect of the invention, means are provided for displaying a symmetrical plot wherein the lowest coordinate is in the center and the plot expands and contracts as the amplitude of the variable increases and decreases.

BRIEF DESCRIPTION OF THE DRAWINGS

FIGS. 3–8 show samples of monitor screens illustrating the method of displaying data in accordance with the invention.

DETAILED DESCRIPTION OF THE INVENTION

Figure 1:
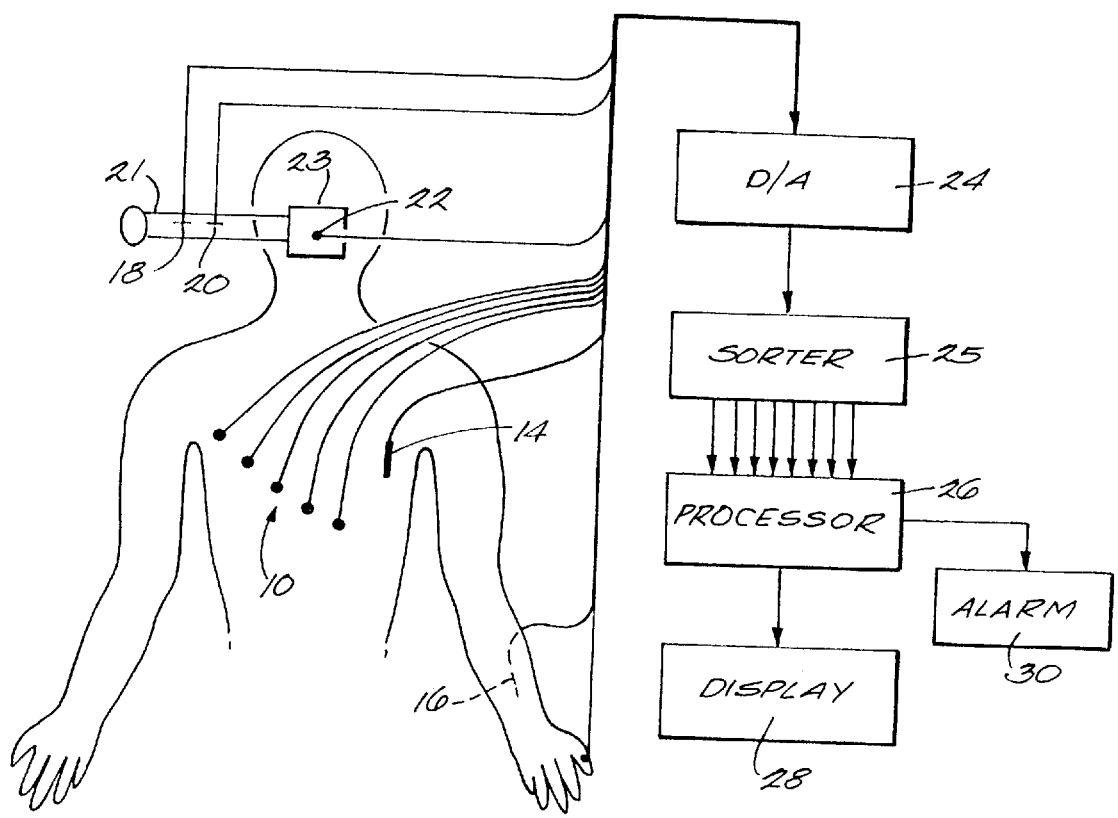
FIG. 1 is a block diagram illustrating the apparatus according to the invention.

FIG. 1 illustrates the display system according to the preferred embodiment of the invention in a medical monitoring application. In particular, the illustrated system is employed in an operating room, for example, and is coupled by an array of sensors to an anesthetized patient. These sensors include, for example, electrodes 10 mounted on the patient's chest for determining electrocardiogram and heart rate, an oximetry sensor 12 mounted on the patient's finger for measuring hemoglobin oxygen saturation, a first catheter 14 for measuring hemoglobin oxygen saturation in the vena cava and central venous pressure, an arterial cannula 16 for measuring arterial systolic and diastolic pressures, a flow meter 18 and a pressure sensor 20 in the endotracheal tube 21 for measuring tracheal gas flow, and airway pressure, respectively, and sensors 22 in the patient's mask 23 for measuring the volume percentage of oxygen and $CO_2$ in the patient's mouth. These signals are first converted from analog to digital by the converter 24 and are then provided to a sorter 25 which sorts the data into rows for display. The rows of data are provided to a processor 26 for computing the functions which are to be displayed. This plot data is then provided to a display 28. If requested, the processor actuates an alarm 30 if any of the data is out of range. Instead of directly displaying the data, it may be stored in the processor's memory or on a disc or tape for later display.

Figure 2A:
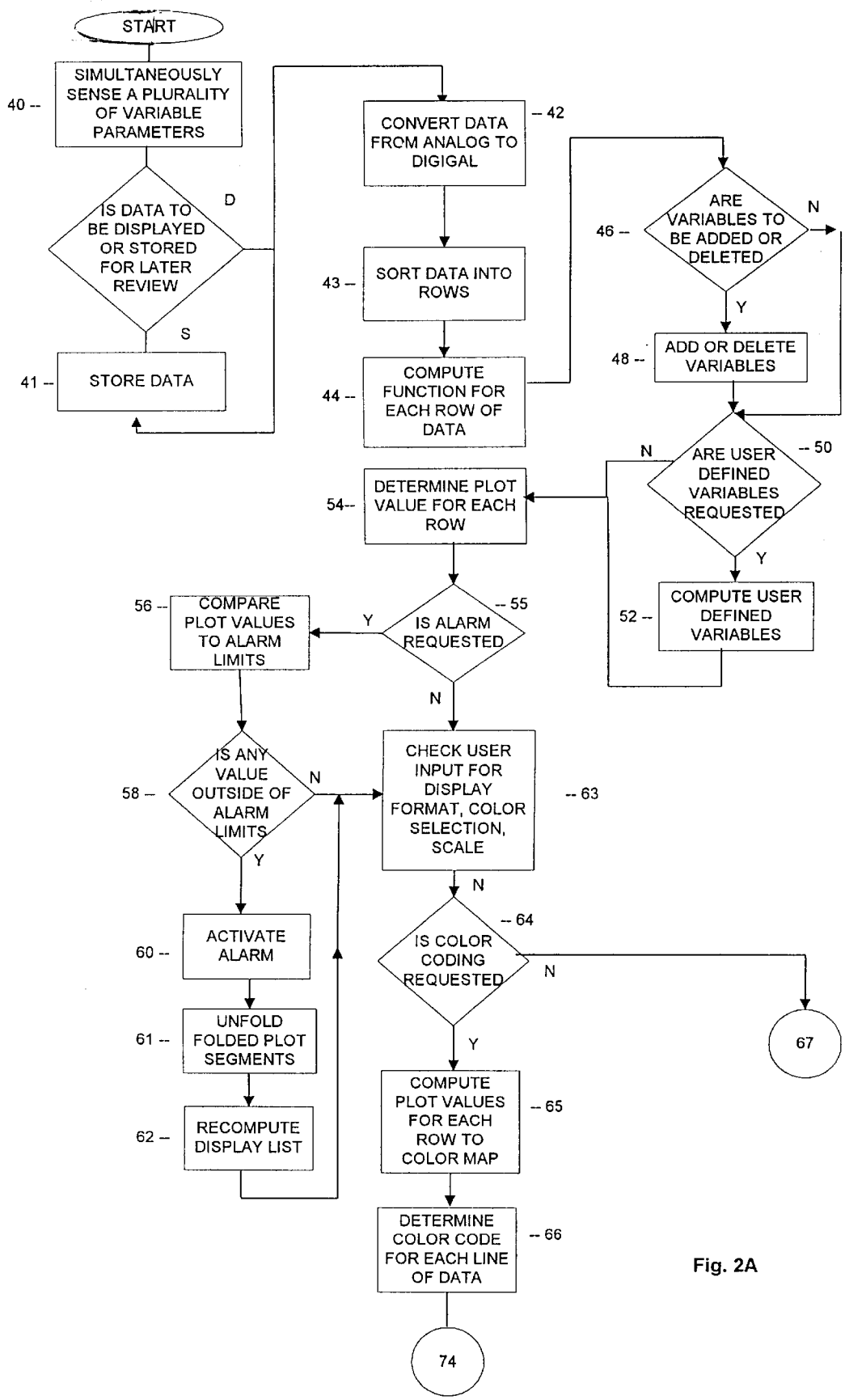
FIGS. 2A, 2B are a flow diagram illustrating the method according to the invention.
Figure 2B:
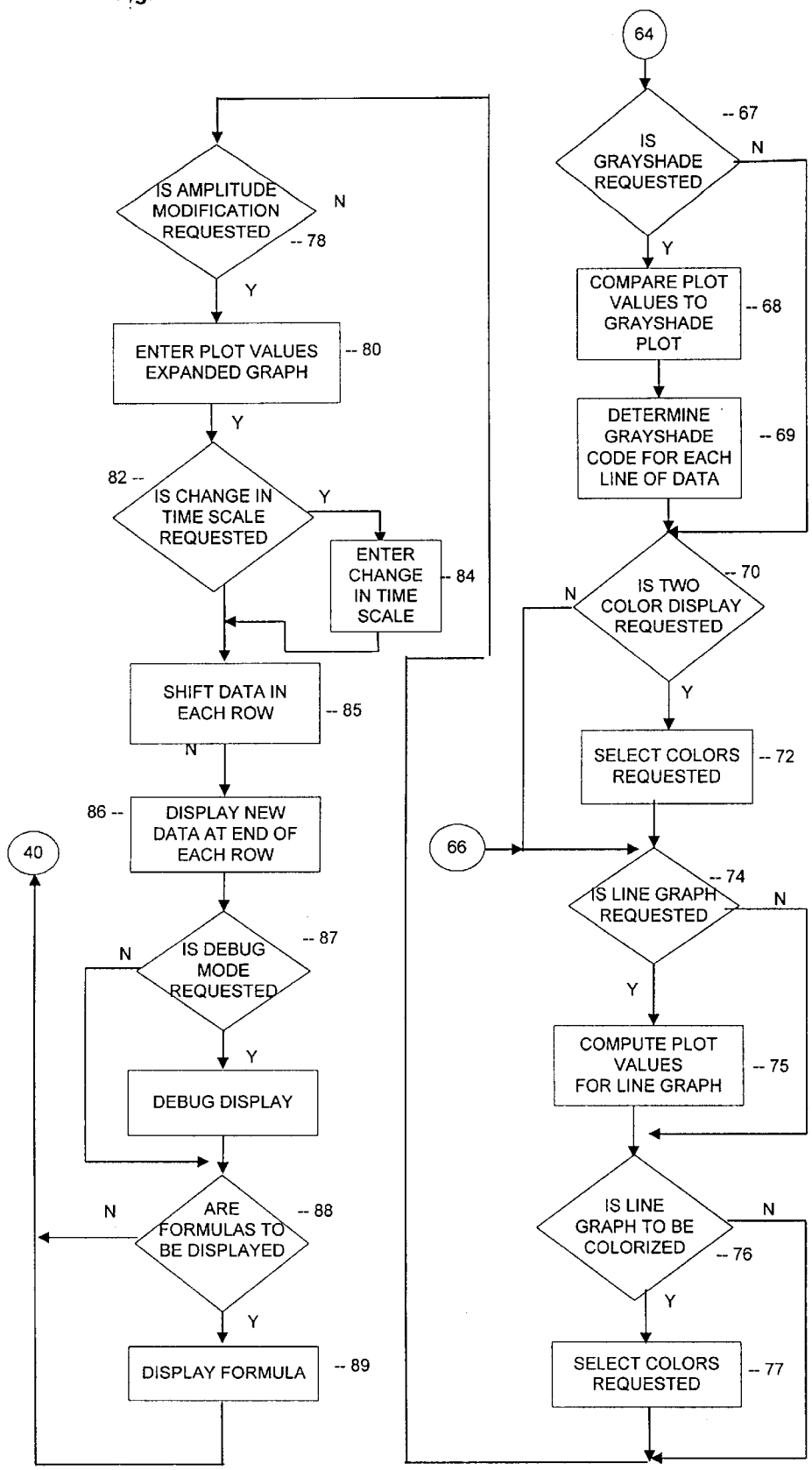

FIG. 2 shows the process according to the preferred embodiment of the invention. Initially at 40, a plurality of variables are simultaneously sensed. This data is either processed immediately or stored in memory 41. In either case, the data received directly from the sensors or previously stored in memory is first converted from an analog signal to digital at 42 and is then sorted into rows at 43. The sorted data is provided to the processor which computes a function for each row of data at 44. Some data, such as arterial systolic and diastolic pressure may be measured directly, although plot value must be determined from the amplitude of electric signals. Other values, such as blood oxygen saturation, must be calculated from known formulas, equations or algorithms expressions. The number of variables sensed may be greater than those actually requested for display at any one time. Therefore, the next step at 46 is to determine whether any variables are to be added to or deleted from the display. These additions or deletions are made at 48. Next, at 50 there is a determination of whether a user defined variable is requested. A user defined variable is a combination of two or more measured variables which are computed, combined or "folded" by the user in accordance with a recognized expression or an arbitrary combination devised by the user and which may indicate a trend in one or more physiologic system groupings. An example of a computed variable is time-tension index which is heart rate times systolic arterial pressure. The plot values for each row of selected or computed data are then determined at 54.

If the display is coupled to an alarm, the system determines if an alarm is requested at 55 and if so, the plot values are compared to alarm limits 56 which determines if the value or a combination of values are outside of the alarm limits and if so an alarm is activated. The user defined functions can also be employed to activate alarms. For example, the most common inter-anesthetic cause of hypoxia is right main stem intubation. If the inspired-end tidal difference is too small, plus there exists an airway pressure greater than predicted, and end tidal $0_2$ and blood oxygen saturation are lower than predicated, hypoxia may exist and a combination of these values may be employed to generate a variable which would actuate an alarm.

If a user-defined variable consists of variables which have been combined or "folded", it is necessary to "unfold" the parameters at 61 and recompute the plot values at 62 so that each may be displayed individually which permits the user to more accurately determine the cause of the alarm signal. Similarly, some variables may be acquired but not displayed at the user's discretion. These variables may also be compared to alarm limits, and if so, will be displayed along with the alarm signal if the signal is outside of the alarm limits.

After the plot value for each row is determined, the system checks the user input for the desired display format, color and scale. In particular, the system determines whether color coding is requested at 64 and if so, at 65 each of the plot values for each row are compared to a color map to provide at 66 a determination of the color code for each line of data. The color map may, for example, be a plurality of colored areas, such as squares in a grid with each square being a different color and represents a value, determined by scaling set by the user.

A typical color map may contain 256 squares which may be any combination of color, shades of a single color or shades of gray. The squares may be defined by the user or the manufacturer. In addition, a single color map may be used for all variables or an individual map may be provided for each variable. For example, the user may wish to indicate a value which is outside the alarm limits by the color red. Thus, red may be high for one variable and low for another with other colors or shades indicating higher or lower values.

The program determines at 67 whether a grayshade or other single color plot is requested. In a manner similar to a multi-color plot, the plot values are compared to a grayshade or single color map at 68 and a grayshade or single color code for each line of data is determined at 69. If neither multi-color, grayshade, nor single color is requested, the program determines at 70 whether a two color display is requested and if so, the requested colors are selected. In addition, the program determines at 74 whether a line graph has been requested either for color, grayshade, single color or two color displays and if so, plot values for a line graph are computed at 75. Also, the program determines at 76 whether the line graph is to be colorized, that is, different colors for high, low and intermediate colors and, if so, this is calculated at 77. Next, the program determines at 78 whether there is a request for a change in amplitude scale at 78 or a change in the time scale is requested at 80, and if either is requested, these values are entered at 82 and/or 84 respectively.

After all of the user inputs have been scanned, the preceding data being displayed in each row is shifted to the right or left at 85. The new data is displayed at the end of the rows at 86 in the format, color scheme and scale requested by the operator. The rows of data are continuously updated and displayed simultaneously in a manner discussed below in connection with FIGS. 3–8.

If the user desires to see the numeric values so that they can be incorporated into the decision making process or for debugging purposes, this decision can be made at 87. If requested, these values are displayed at 87 as rows of numerical data instead of colorized bars. In addition, mathematical formulas used to compute the value will also be displayed at 88, 89, if desired.

FIGS. 3–8 show samples of monitor screens illustrating the method of displaying data in accordance with the invention. These figures also illustrate an example of data which might be displayed on an operating room monitor, for example. However, it is to be understood that the indicated data is for purposes of illustration only and is not intended to be inclusive. The operator can add other variables and delete some or all of those shown. Also, any variable can be moved, hidden or displayed at the user's discretion. As a result, the operator can view as many or as few variables at any given time as may be appropriate. In addition, the user can display or hide variables by clicking on the appropriate folder.

Figure 3:
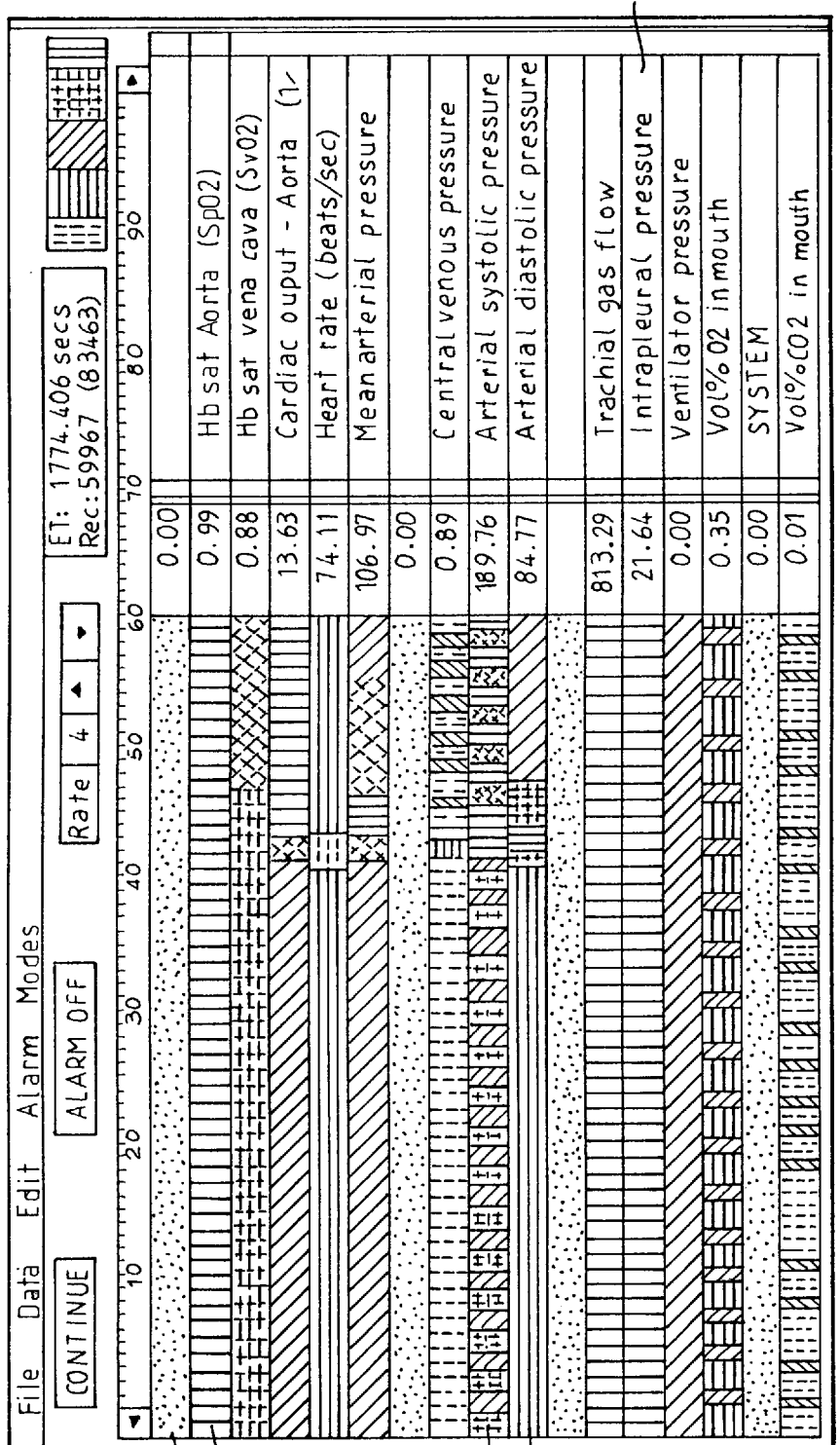

The screen of FIG. 3 lists the variables being displayed in a column 100 at the right; the current values of each of the variables are displayed in a second column 102; and the data plotted in a colorized code in the window 104 at the left. The current value appearing in column 102 corresponds to the value at the end of the row from which the bar is moving. In the illustrated example, the bars are moving from left to right on the same time base as new data is entered at the left. It will be appreciated, however, that the data can be moved in either direction.

The variables may be arranged by systems. In the illustrated embodiment, variables relating to the circulation system are listed under that heading in column 100 and variables relating to the respiration system are listed under that heading.

Any color code can be employed to show variations in amplitude. In the example illustrated in FIG. 3, the rainbow colors of red, orange, yellow, green, blue, indigo and violet are employed with red indicating high values, violet indicating low values with the other colors indicating intermediate values in the order shown. Therefore, in the illustrated example, the color of the cardiac output plot 106 changes from red to orange to green indicating a decrease from a relatively high level to an intermediate level. Also, the heart rate plot 108 changes in color from green to yellow to indigo, indicating an increase and then a decrease to a lower steady state. The plot for arterial systolic pressure 110 changes from alternating red and orange to red and then to alternating green and yellow and the arterial diastolic pressure plot 112 changes from green to yellow, red, yellow and finally a steady state blue. The occurrence of each of these changes at approximately the same time indicates the occurrence of an "event" for which some attention may be required or the result of some action such as the administering of a drug. This change in condition would become immediately apparent to the operator through the abrupt color changes. Thus, the operator would become more readily aware of the occurrence of the "event" than would be the case if the data were displayed solely graphically or numerically. In addition to striking events, subtle trends can be detected more easily. Also, if one of a number of variables changes, the eye is immediately attracted to that variable at the time of its change.

The variables shown in FIG. 3 are examples only. The operator may choose the variables to be displayed from a menu. Variables may be added, deleted or the variables can be rearranged, put into file folders or new file folders created. variables can be rearranged, put into file folders or new file folders created.

With stored data, the rate that the data is updated and entered at the left margin in FIG. 3 can be set by the operator and is a function of compression. The more the horizontal scale is compressed, the faster that the stored data is moved across the screen. The compression scale is shown by the bar 113 in FIG. 3.

FIG. 4 illustrates a partial screen illustrating substantially the same information as FIG. 3, although not necessarily the same values, except that the information is both color coded and illustrated by line graphs. This would be the result of the selection of both color coding at 64 and the line graph at 74 in FIG. 2. Thus, the operator would be advised regarding variations in the magnitude of the signals both by changes in color and changes in the amplitude of the line graph. This makes trends or abrupt changes in the condition of a system even more readily apparent and the combination aids in assessing the magnitude and direction of the change.

Figure 5:
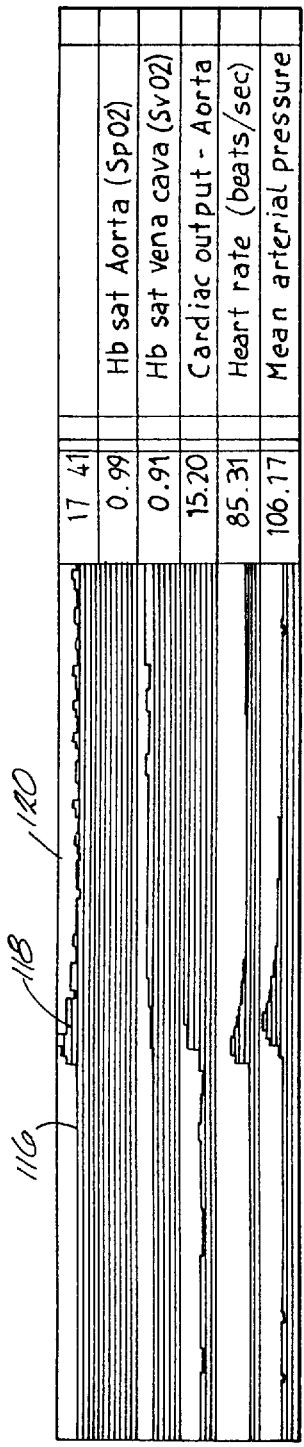

FIG. 5 is a partial screen showing an alternate manner of illustrating the data in which a line graph 116 is employed with the area 118 below the line being one color in the background 120 a second color so as to highlight both the magnitude of the signals and the occurrence of abrupt changes. This would be the result of selecting two color displays at 70 and a line graph at 74 of FIG. 2.

FIG. 5 also illustrates another aspect of the invention wherein the number 17.41 appears opposite the heading System 0. This is an arbitrary parameter selected by the operator and may be derived, for example, by a mathematical computation involving two or more of the values in the system which appears below it. This user defined variable permits the user to look at a few composite variables derived from a larger number of mathematical functions. As a result, the composite variable or envelope display 122 can comprise a single bar or plot which reflects what is happening within the variables that it contains. A simple example of a user defined variable is the time-tension index, which is heart rate times systolic arterial pressure.

Figure 6:
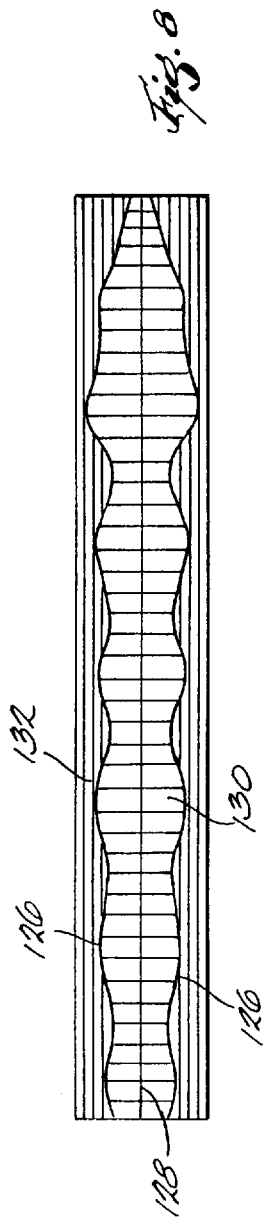

FIG. 6 is a partial screen showing an alternate method of illustrating the information according to the invention wherein the bar graphs are limited to two colors, which in the illustrated example are red and green. While any combination of colors can be employed, in the illustrated example, the key, not shown, would indicate that red is within limits and that green is outside the limits. This permits the operator to instantly scan the various parameters and determine which are within and which are outside the limits. As another example, a third color could be added, such as yellow, which would indicate caution, e.g., an impending change or approach from inside to outside the limits.

FIG. 7 shows a partial screen illustrating an alternate method of illustrating the data wherein the information is displayed in shades of gray with the color code in the upper right indicating that white is high and black is low with shades of gray indicating intermediate values. Another method of illustrating the magnitude of data using two colors is for one color to indicate a maximum value, the second color to indicate a minimum value and shades of the colors to indicate intermediate values.

FIG. 8 illustrates an alternate method of displaying data wherein a symmetrical plot 126 is used. This is a plot wherein the values are plotted as both a plus and a minus around a base line 128. The area 130 with the plot is coded in one color and the background 132 in another.

Those skilled in the art will appreciate that the illustrated color codes are merely meant as examples. With the system according to the invention, the operator can select or develop any color code which illustrates variations in the data. Moreover, the time scale can be compressed to indicate trends or expanded so as to indicate individual heart beats. In addition, the amplitude scale of any of the individual displays may also be modified by the user.

Also, while the invention is illustrated in connection with a medical monitor, it may employed for monitoring the operation of other complicated systems with a large number of variables, such as, aircraft, flight control tower systems, nuclear power plants, electrical grids, and complex industrial manufacturing or processing operations.

We claim:

1. A combination for simultaneously displaying a plurality of time variables indicative of the condition of a dynamic system, the combination being constructed and arranged to be coupled to a source of discreet signals each functionally related to one of the variables, said combination comprising means for receiving said signals and for generating a plurality of time variable values each of which is indicative of one of said signals, means for converting each of said time variable values into color codes, means for separately and simultaneously displaying each of said time varying color coded values in a graphic form on a display screen in a time correlated relation wherein variations in said values are emphasized by differences in color or shade.

2. The combination set forth in claim 1 and including means for varying the color of each of the displayed time variable values in relation to the magnitude of the signal, the signals being displayed in separate colorized bars wherein the magnitude of each variable determines the shade of color.

3. The combination set forth in claim 1 wherein the variable are plotted graphically in a plot line form to define areas above and below the plot line, and mean for applying one color in the area above the plot line and a different color in the area below the plot line.

4. A combination comprising means for simultaneously sensing data representing a plurality of variables, means for sorting the sensed data into rows, means for determining plot data for each row of data, means for color coding the plot data for each row of data and means for displaying color coded rows of data plot on a time base.

5. The combination set forth in claim 4 and including means for computing plot values of each of said variables as a line graph and means for plotting each row of data with a color code and a line graph so that changes in amplitude of the variables appear as changes in amplitude of the line graph and changes in the shade of color.

6. The combination set forth in claim 4 and including means for computing a system variable from one or more sensed variables said means for displaying being operative to display said computed variable as a separate row of data.

7. The combination set forth in claim 4 and including means for comparing plot values to alarm limits and means for activating an alarm when the plot values are outside of alarm limits.

8. The combination set forth in claim 4 and including means for determining upper and lower limits for each row of data, and means for displaying data within the limits as one color and data outside of the limits as a second color.

9. The combination set forth in claim 4 and including means for displaying changes in amplitude of the data as varying shades of gray.

10. The combination set forth in claim 4 wherein said means for color coding includes means for displaying changes in the amplitude in the data as variations in the visible color spectrum consisting of the colors red, orange, yellow, green, blue, indigo and violet.

11. The combination set forth in claim 4 and including means for simultaneously moving the displayed color coded rows of data across a display screen and adding new data at the end of the rows from which the data is moving.

12. The combination set forth in claim 11 including means for computing plot values of each of said variables as a line graph, and means for plotting each row of data with a color code and line graph so that changes in amplitude of the variable appear as changes in amplitude of the line graph and shade of color.

13. The combination set forth in claim 12 wherein said means for color coding includes means for displaying changes in the amplitude in the data as variations in a color scale consisting of the colors red, orange, yellow, green, blue, indigo and violet.

14. The combination set forth in claim 13 and including means for computing a system variable from one or more sensed variables, said means for displaying being operative to display said computed variable as a separate row of data.

15. The combination set forth in claim 14 and including means for comparing plot values to alarm limits and means for activating an alarm when the plot values are outside of alarm limits.

16. A method of simultaneously displaying a plurality of time variable parameters, including the steps of simultaneously acquiring a plurality of streams of data representative of variables, sorting the sensed data into rows, determining plot data for each row of data, converting each of said plot values into a color code, and displaying color coded rows of data on a time base.

17. The method set forth in claim 16 including the steps of computing plot values of each of said variables as a line graph, and plotting each row of data with a color code and line graph so that changes in amplitude of the parameter appear as changes in amplitude of the line graph and shade of color.

18. The method set forth in claim 16 and including the step of computing a system variable from one or more sensed variables and displaying said computed variable as a separate row of data.

19. The method set forth in claim 16 and including the steps of comparing plot values to alarm limits and activating an alarm when the plot values are outside of alarm limits.

20. The method set forth in claim 19 wherein at least one of the plot values is not displayed, comparing said undisplayed plot value to at least one alarm limit, and displaying said previously undisplayed variable if said variable exceeds the alarm limit.

21. The method set forth in claim 16 and including the steps of determining upper and lower limits for each line of data, and displaying data within the limits as one color and data outside of the limits as a second color.

22. The method set forth in claim 16 and including the steps of displaying changes in amplitude of the data as varying shades of a single color.

23. The method set forth in claim 16 and including the steps of displaying changes in the amplitude in the data as variations in a color scale consisting of the colors red, orange, yellow, green, blue, indigo and violet.

24. The method set forth in claim 16 and including the steps of simultaneously moving the rows of displayed data across a display screen, and adding new data to the end of each row from which the row of data is moving.

25. The method set forth in claim 24 and including the step of comparing each plot value to a color map in which different color shades are designated for numeric values of said variables, determining a color code for each variable, and displaying said color coded values.

26. The method set forth in claim 25 including the steps of computing plot values of each of said parameters as a line graph, and plotting each row of data with a color code and line graph so that changes in amplitude of the parameter appear as changes in amplitude of the line graph and shade of color.

27. The method set forth in claim 26 and including the steps of displaying changes in the amplitude in the data as variations in a color scale consisting of the colors red, orange, yellow, green, blue, indigo and violet.

28. The method set forth in claim 27 and including the step of computing a system variable from one or more sensed variables and displaying said computed variable as a separate row of data.

29. The method set forth in claim 27 and including the steps of comparing plot values to alarm limits and activating an alarm when the plot values are outside of alarm limits.

30. The method set forth in said claim 29 wherein at least one of the plot values is not displayed, comparing said undisplayed plot value to at least one alarm limit, and displaying said previously undisplayed variable if said variable exceeds the alarm limit.

31. A combination for simultaneously displaying a plurality of time variables indicative of the condition of a dynamic system, the combination being constructed and arranged to be coupled to a source of discreet signals each functionally related to one of the variables, said combination comprising a processor for receiving said signals and for generating a plurality of time variable values each of which is indicative of one of said signals, said processor being programmed to convert each of said time variable values into color codes, and a display constructed and arranged to separately and simultaneously display each of said time varying color coded values in a graphic form on a display screen in a time correlated relation wherein variations in said values are emphasized by differences in color or shade.

32. The combination set forth in claim 31 wherein said processor is programmed to vary the color of each of the displayed time variable values in relation to the magnitude of the signal, the signals being displayed in separate colorized bars wherein the magnitude of each variable determines the shade of color.

33. The combination set forth in claim 31 wherein the variable are plotted graphically in a plot line form to define areas above and below the plot lines, said processor being programmed to color code the data to be displayed with one color in the area above the plot line and a different color in the area below the plot line.

34. A combination comprising sensors constructed and arranged to simultaneously sense data representing a plurality of variables, a sorter constructed and arranged to sort the sensed data into rows, a processor programmed to determine plot data for each row of data and to color code the plot data for each row of data and a display coupled to the processor and constructed and arranged to display the color coded rows of data on a time base.

35. The combination set forth in claim 34 wherein the processor is programmed to compute plot values of each of said variables as a line graph and to plot each row of data with a color code and a line graph so that changes in amplitude of the variables appear as changes in amplitude of the line graph and changes in the shade of color.

36. The combination set forth in claim 34 wherein said processor is programmed to compute a system variable from one or more sensed variables said display being operative to display said computed variable as a separate row of data.

37. The combination set forth in claim 34 and wherein said processor is programmed to compare plot values to alarm limits and to activate an alarm when the plot values are outside of alarm limits.

38. A combination set forth in claim 34 and wherein said processor is programmed to determine upper and lower limits for each row of data, said display being operative to display data within the limits as one color and data outside of the limits as a second color.

39. The combination set forth in claim 34 wherein said processor is programmed to color code changes in amplitude of the data as varying shades of gray.

40. The combination set forth in claim 34 wherein said processor is programmed to color code changes in the amplitude of the data as variations in the visible color spectrum consisting of the colors red, orange, yellow, green, blue, indigo and violet.

41. The combination set forth in claim 34 wherein said processor is programmed to simultaneously move the displayed color coded rows of data across a display screen and to add new data at the end of the rows from which the data is moving.

42. The combination set forth in claim 41 wherein said processors is programmed to compute plot values of each of said variables as a line graph, and to plot each row of data with a color code and line graph so that changes in amplitude of the a variable appears as changes in amplitude of the line graph and shade of color.

43. The combination set forth in claim 42 wherein said processor is programmed to display changes in the amplitude in the data as variations in a color scale consisting of the colors red, orange, yellow, green, blue, indigo and violet.

44. The combination set forth in claim 43 and wherein said processor is programmed to compute a system variable from one or more sensed variables, said display being operative to display said computed variable as a separate row of data.

45. The combination set forth in claim 44 wherein said processor is programmed to compare plot values to alarm limits and to activate an alarm when the plot values are outside of alarm limits.

* * * * *